US00PP28789P3

(12) United States Plant Patent
Brand

(10) Patent No.: US PP28,789 P3
(45) Date of Patent: Dec. 26, 2017

(54) ***ARONIA* PLANT NAMED 'UCONNAM165'**

(50) Latin Name: *Aronia melanocarpa*
Varietal Denomination: UCONNAM165

(71) Applicant: University of Connecticut, Farmington, CT (US)

(72) Inventor: Mark Henry Brand, Willington, CT (US)

(73) Assignee: University of Connecticut Technology Commerialization Services, Farmington, CT (US)

( * ) Notice: Subject to any disclaimer, the term of this patent is extended or adjusted under 35 U.S.C. 154(b) by 31 days.

(21) Appl. No.: 14/998,770

(22) Filed: Feb. 10, 2016

(65) Prior Publication Data

US 2017/0231135 P1 Aug. 10, 2017

(51) Int. Cl.
*A01H 5/00* (2006.01)

(52) U.S. Cl.
USPC ..... Plt./156

(58) Field of Classification Search
USPC ..... Plt./226, 156
CPC ..... A01H 5/02; A01H 5/00; A01H 5/2016
See application file for complete search history.

(56) References Cited

PUBLICATIONS

Missouri Botanical Garden *Aronia melanocarpa* 'Morton' Iroquiois Beauty retrieved on May 8, 2017, retrieved from the Internet at <http://www.missouribotanicalgarden.org/PlantFinder/PlantFinderDetails.aspx?kempercode=c622> 2 pp.*

Proven Winners Low Scape Mound *Aronia melanocarpa* 2017, retrieved on May 8, 2017, retrieved from the Internet at <https://www.provenwinners.com/plants/aronia/low-scape-mound-aronia-melanocarpa> 3 pp.*

Spring Meadow Nursery Flowering Shrubs Starter Plants Catalog and Shrub Reference 2015-2016, retrieved on May 8, 2017, retrieved from Internet at <http://springmeadownursery.com/content-media/catalog_2015.pdf> pp. 1-6, 12, 33 and 100.*

* cited by examiner

*Primary Examiner* — June Hwu
(74) *Attorney, Agent, or Firm* — Cassandra Bright

(57) ABSTRACT

A new and distinct *Aronia* cultivar named 'UCONNAM165' is disclosed, characterized by a compact, dense plants maturing to approximately 2 feet tall and 3 to 4 feet wide. Foliage is uniquely small and very shiny, emerging with a red tinge, green throughout the Spring and Summer, turning red and orange in the Fall. Plants are very useful for landscape, with a short, controlled growth and tolerating a wide range of soil conditions. Profuse flowering. The new variety is a *Aronia*, normally produced as an outdoor garden or container plant.

2 Drawing Sheets

Figure 1:
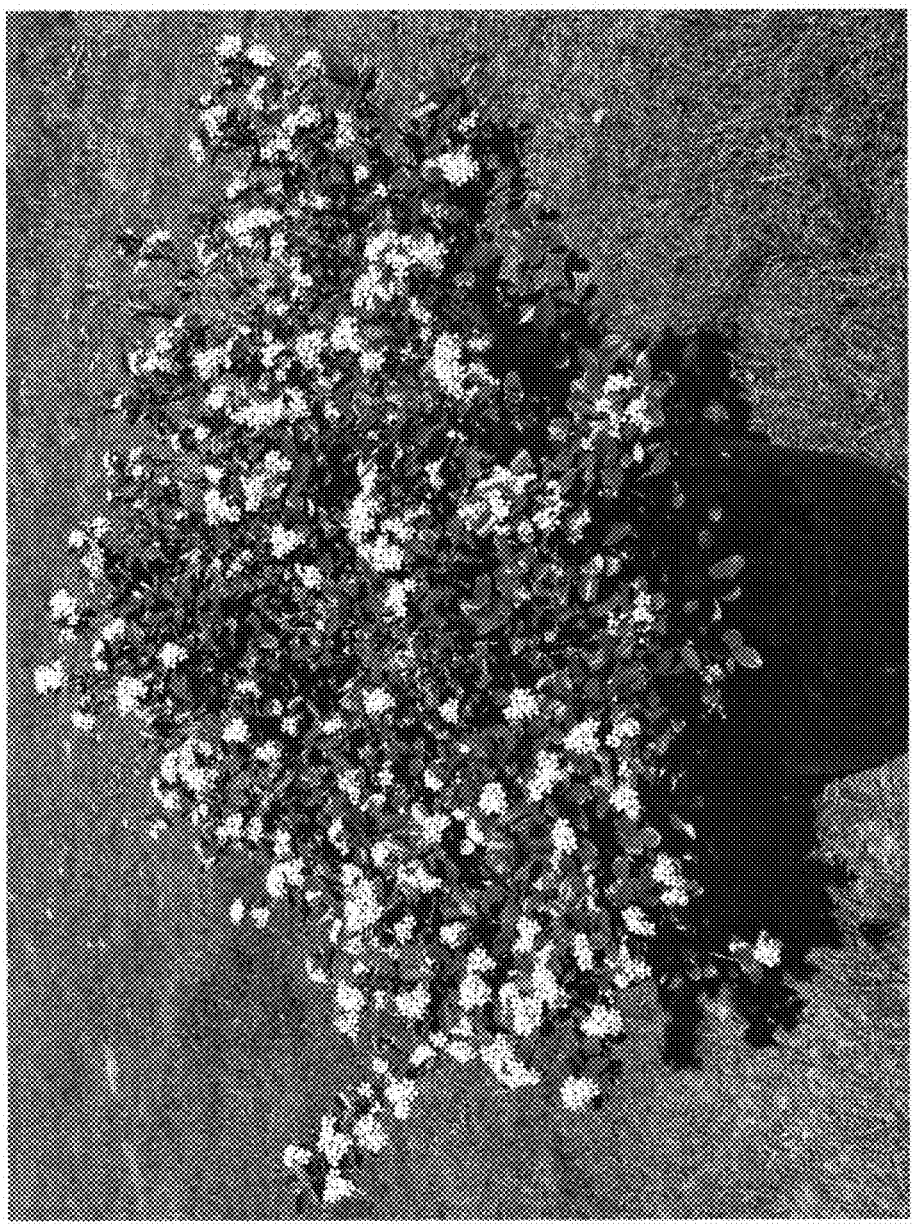

This invention was made with government support under grant number 58-1230-7-439 awarded by the United States Department of Agriculture. The government has certain rights in the invention.

Latin name of the genus and species: *Aronia melanocarpa.*

Variety denomination: 'UCONNAM165'.

BACKGROUND OF THE INVENTION

The new *Aronia* cultivar is a product of a planned breeding program conducted by the inventor, Mark Henry Brand in Storrs, Conn. The objective of the breeding program was to produce new *Aronia* varieties that are low growing, compact plants with substantial bloom, high quality summer foliage and colorful fall foliage as well as novel growth forms of *Aronia*. The cross resulting in this new variety was made during May of 2006.

The seed parent is the, unpatented, commercial variety referred to as *Aronia melanocarpa* 'UC012'. The pollen parent is the unpatented, commercial variety referred to as *Aronia melanocarpa* 'UC017'. The new variety was discovered in May of 2011 by the inventor in a group of seedlings resulting from the 2006 crossing, in a greenhouse in Storrs, Conn.

Asexual reproduction of the new cultivar 'UCONNAM165' by tissue culture, using nodal initiation, was first performed during June of 2011, at a laboratory in Storrs Conn. Subsequent propagation by softwood cuttings has shown that the unique features of this cultivar are stable and reproduced true to type in 4 successive generations.

SUMMARY OF THE INVENTION

The cultivar 'UCONNAM165' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'UCONNAM165' These characteristics in combination distinguish 'UCONNAM165' as a new and distinct *Aronia* cultivar:

1. Very dense, compact plants that mature to 2' tall by 3-4' wide. Shoots are upright
2. Leaves emerge red tinged, then mature to shiny dark green. Leaves are smaller than typical for *Aronia.*
3. Fall foliage color is red with orange mixed in.
4. Profuse clusters of small white flowers in early May (Connecticut). Small black berries in August.

5. Can grow in full sun or partial shade and is tolerant of challenging landscape situations including dry soils, once established.
6. Dense, compact form is useful in smaller landscapes and where large shrubs are unwanted.
7. Multi-season interest from spring flowers, excellent glossy summer foliage, summer fruits and red-orange fall foliage color.
8. Excellent for durable mass plantings or low hedges.
9. Very shiny foliage.

PARENT COMPARISON

Plants of the new cultivar 'UCONNAM165' are similar to plants of the seed parent, *Aronia melanocarpa* 'UC012' in most horticultural characteristics, however, plants of the new cultivar 'UCONNAM165' differ in the following;

1. Mature size of 2 feet tall by 3 to 4 feet wide, whereas the seed parent is 1 to 2 feet tall and 3 to 4 feet wide.
2. Very dense, compact, upright habit, whereas the seed parent is prostrate, with a highly rhizomatous growth habit.
3. Very dense flowering, whereas the seed parent is moderately dense flowering.
4. Very shiny foliage, dark green, whereas the seed parent has moderately shiny foliage.

Plants of the new cultivar 'UCONNAM165' are similar to plants of the pollen parent, *Aronia melanocarpa* 'UC017' in most horticultural characteristics, however, plants of the new cultivar 'UCONNAM165' differ in the following;

1. Mature size of 2 feet tall by 3 to 4 feet wide, whereas the pollen parent is 6 to 8 feet tall and 6 to 8 feet wide.
2. Very dense, compact, upright habit, whereas the pollen parent is of somewhat loose, open spreading form.
3. Very dense flowering, whereas the pollen parent is moderately dense flowering.

COMMERCIAL COMPARISON

Plants of the new cultivar 'UCCONNAM165' can be compared to the unpatented commercial variety *Aronia* 'Morton' (aka 'Iroquois Beauty'). These varieties are similar in most horticultural characteristics; however, 'UCONNAM165' differs in the following:

1. Very dense habit, whereas the comparator is moderately dense in habit.
2. Red-orange fall foliage color, whereas the comparator has an orange-yellow fall foliage color.
3. Profuse amounts of white flower clusters, whereas the comparator has moderate amounts of white flower clusters.
4. Foliage is extremely shiny, whereas the comparator has foliage that is not shiny.

Plants of the new cultivar 'UCONNAM165' can also be compared to the unpatented commercial variety *Aronia* 'Autumn Magic'. These varieties are similar in most horticultural characteristics; however, 'UCONNAM165' differs in the following:

1. Mature size of 2 feet tall by 3 to 4 feet wide: very dense habit, whereas the comparator is 5 to 6 feet tall and 5 to 7 feet wide; moderately dense habit.
2. Red-orange fall foliage color, whereas the comparator has an orange-yellow fall foliage color.
3. Profuse amounts of white flower clusters, whereas the comparator has moderate amounts of white flower clusters.
4. Foliage is extremely shiny, whereas the comparator has foliage that is not shiny.

BRIEF DESCRIPTION OF THE PHOTOGRAPHS

The accompanying photograph in FIG. 1 illustrates in full color a typical plant of 'UCONNAM165' shown in a 3 gallon commercial container overwintered in an unheated hoop house, in Mansfield, Conn.

Figure 2:
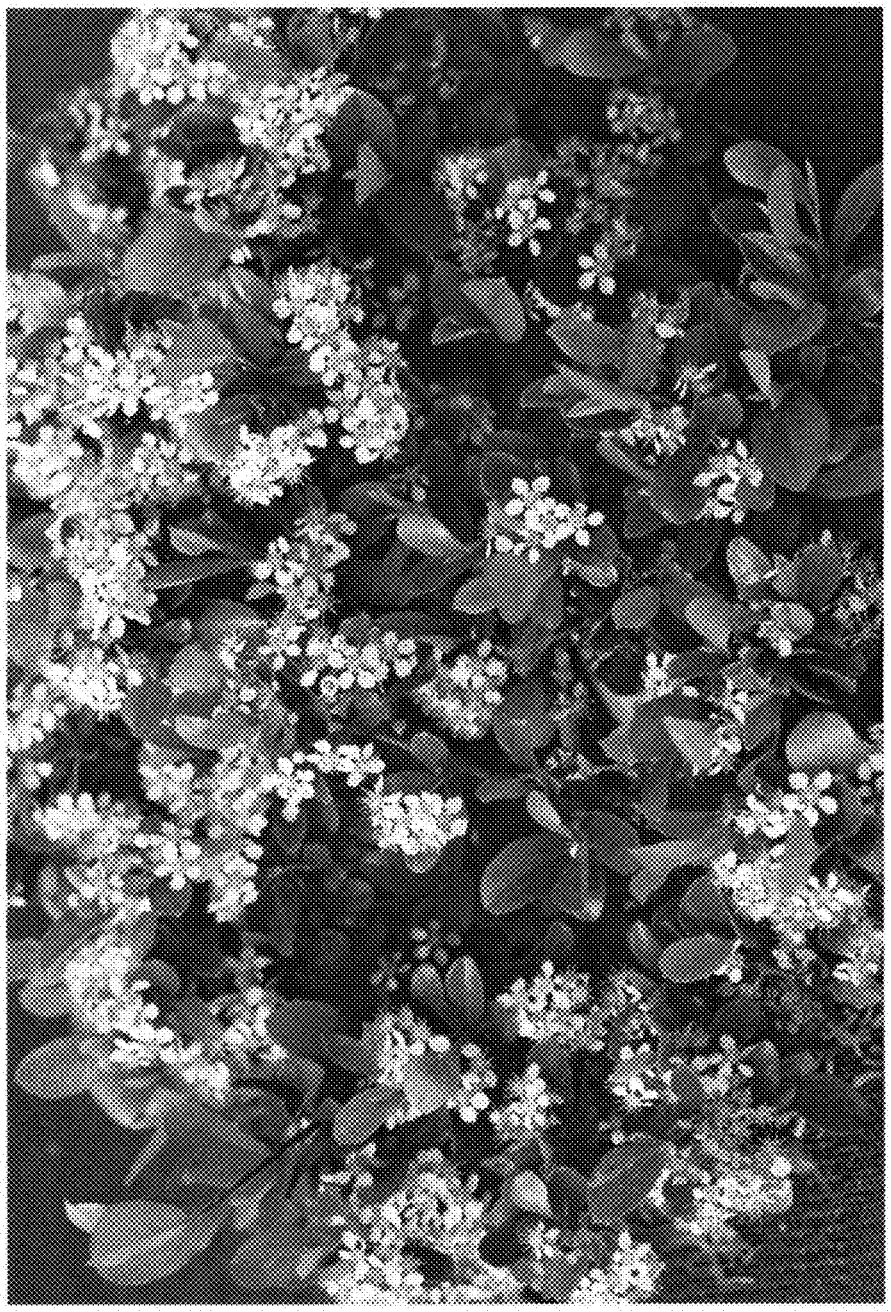

FIG. 2 illustrates in full color a close up of typical inflorescence and foliage of 'UCONNAM165'. Age of the plant photographed is approximately 6 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'UCONNAM165' plants grown in poly house in Grand Haven, Mich., under natural lighting. Measurements were taken during April of 2015. The plants were 2-3 years old in 3 gallon containers. The growing temperature ranged from 5° C. to 27° C. Measurements and numerical values represent averages of typical plant types.

Botanical classification: *Aronia melanocarpa* 'UCONNAM165'.

PROPAGATION

Time to initiate roots: About 3 weeks at approximately 24° C.

Time to produce a rooted young plant: About 8 weeks at 24° C.

PLANT

Plant type: Perennial shrub.
Age of plant described: Approximately 2 to 3 years old.
Growth habit: Low rounded/spreading.
Pot size of plant described: 3 gallon pot.
Appropriate containers sizes: 1, 2 and 3 gallon commercial containers.
Overall plant shape: Compact spreading globular form.
Height: 60-65 cm.
Plant spread: 62-70 cm.
Growth rate: Moderate.
Plant vigor: Good.
Branching characteristics: Low branching, some basal branching.
Length of primary lateral branches: 50 cm.
Diameter of lateral branches: 5 mm.
Quantity of lateral branches: About 15.
Internode length: About 3 cm.
Stem:

*Stem appearance*.—Round.
*Stem strength*.—Moderate.
*Stem color*.—New growth: Near RHS Greyed-Orange 176B. 1-year-old growth: Near RHS Yellow-Green 152B. Old Growth: Near RHS Greyed-Green 197A.
*Pubescence*.—Present on new growth.
*Angle of attachment*.—About 45° angle of attachment.

Other plant characteristics: Lenticels: 1 mm Near RHS Greyed-Orange 177B.

Roots: Moderate density moderate branching. Medium thickness, fibrous and white in color, not accurately measured with R.H.S. Chart.

FOLIAGE

Leaf:

*Arrangement*.—Alternate, single.

*Leaf shape*.—Young: Elliptic. Mature: Obovate.

*Average length*.—4 cm.

*Average width*.—2.5 cm.

*Apex*.—Immature foliage acute to acuminate, mature foliage rounded.

*Base*.—Cuneate.

*Margin*.—Crenate.

*Texture of top surface*.—Smooth, very shiny.

*Texture of bottom surface*.—Slightly rough/waxy.

*Leaf side with pubescence*.—Slightly on under side.

*Color*.—Young foliage upper side: Near RHS Yellow-Green 143A, tinged Red 42B along margin. Young foliage under side: Near RHS Yellow-Green 146C, tinged Red 42B along margin. Mature foliage upper side: Near RHS Green 139A. Mature foliage under side: Near RHS Yellow-Green 148B.

*Fall foliage*.—Upper side: Near RHS Orange N25C, flushed Red 45D. Under side: Near RHS Orange N25C, flushed Red 45D.

*Venation*.—Pattern: Pinnate. Color upper side: Midrib: Near RHS Yellow-Green 145A. Lateral Veins: Near RHS Green 143A. Color under side: Midrib: Near RHS Yellow-Green 145A. Lateral Veins: Near RHS Yellow-Green 148B.

*Petiole*.—Average Length: 3 mm. Diameter: 1 mm. Petiole color upper side: Near RHS Yellow-green 145A. Petiole color lower side: Near RHS Yellow-green 145A. Petiole Texture upper side: Smooth/waxy. Petiole Texture lower side: Smooth/waxy.

FLOWER

Natural flowering season: Spring.

Flower arrangement: Corymb.

Inflorescence type and habit: Compound corymb, composed of outwardly facing flowers.

Inflorescence height: 2-3 cm.

Inflorescence width: 2-3 cm.

Quantity of flowers per inflorescence: 3-15.

Quantity of flowers per lateral stem: 25-40.

Quantity of flowers per plant: 45-60.

Flower longevity on plant: 1-2 weeks.

Individual flowers:

*Flower form*.—Rotate.

*Flower shape*.—Radial.

*Flower aspect*.—Upright.

Size:

*Diameter*.—12 mm.

*Length*.—12 mm.

*Depth*.—6 mm.

Flower other characteristics:

*Persistence*.—Self cleaning.

*Fragrance*.—Very slight.

Petal:

*Petal arrangement*.—Whorled.

*Petal appearance*.—Spade-like.

*Number of petals per flower*.—5.

*Petal fused*.—No.

*Petal shape*.—Circular.

*Petal base*.—Attenuate.

*Margin*.—Entire.

*Tip shape*.—Rounded.

*Length*.—5 mm.

*Width*.—4 mm.

*Texture*.—Upper: Glabrous. Lower: Glabrous.

Petal color:

*When opening*.—Upper surface: Near RHS White 155B. Lower surface: Near RHS White 155B with a blush of Red-Purple 62C.

*Fully opened*.—Upper surface: Near RHS White 155B. Lower surface: Near RHS White 155B.

Bud:

*Shape*.—Spherical.

*Length*.—5 mm.

*Diameter*.—4 mm.

*Color*.—Near RHS White 155B and Greyed-Purple 186B.

Calyx:

*Shape*.—Radial.

*Length*.—3 mm.

*Diameter*.—5.5 mm.

Sepals:

*Arrangement*.—Radial.

*Number*.—5.

*Shape*.—Broad deltate.

*Base*.—Truncate.

*Margin*.—Entire.

*Tip shape*.—Acute.

*Length*.—1 mm.

*Width*.—1 mm.

*Color upper*.—Near RHS Green 139D.

*Color lower*.—Near RHS Green 139C.

*Texture*.—Upper: Pubescent. Lower: Glabrous.

Peduncle:

*Length*.—7 mm.

*Diameter*.—1 mm.

*Color*.—Near RHS Yellow-Green 146D.

*Strength*.—Good.

*Texture*.—Glabrous.

REPRODUCTIVE ORGANS

Stamens:

*Number*.—18.

*Filament length*.—4 mm.

*Filament color*.—Near RHS White 155B.

Anthers:

*Shape*.—Dorsifixed.

*Length*.—1 mm.

*Color*.—Near RHS Red-Purple 59B.

*Pollen color*.—Brown.

*Pollen amount*.—Scant to moderate.

Pistil:

*Number*.—4.

*Length*.—3 mm.

*Style*.—Length: 1 mm. Color: Near RHS Yellow-Green 146D.

*Stigma*.—Shape: Syncarpous fused stigma with 3-5 lobes. Color: Near RHS Yellow-Green 146D. Ovary Color: Near RHS Yellow-Green 146D.

OTHER CHARACTERISTICS

Fruit: Produced in late Summer. Small pome. Not produced abundantly. 3 to 7 clustered together. Colored near Greyed-Purple N186A of nearly Black 202A. Glossy. Average 8 mm diameter. Fruit petiole 1 to 2 cm long, weak, slightly pubescent colored near Greyed-Red 180B.

Disease/pest resistance: Typical of the species.

Temperature tolerance: The new variety tested to temperatures between −25° C. to 40° C.

What is claimed is:

1. A new and distinct cultivar of *Aronia* plant named 'UCONNAM165' as herein illustrated and described.

* * * * *